US009301378B2

(12) United States Patent
Steadman Booker et al.

(10) Patent No.: US 9,301,378 B2
(45) Date of Patent: Mar. 29, 2016

(54) PHOTON COUNTING DETECTOR (71) Applicant: KONINKLIJKE PHILIPS N.V., Eindhoven (NL)

(72) Inventors: Roger Steadman Booker, Aachen (DE); Randall Peter Luhta, Chardon, OH (US); Christoph Herrmann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 180 days.

(21) Appl. No.: 14/350,370

(22) PCT Filed: Oct. 12, 2012

(86) PCT No.: PCT/IB2012/055554
§ 371 (c)(1),
(2) Date: Apr. 8, 2014

(87) PCT Pub. No.: WO2013/057645
PCT Pub. Date: Apr. 25, 2013

(65) Prior Publication Data
US 2014/0254749 A1 Sep. 11, 2014

Related U.S. Application Data

(60) Provisional application No. 61/548,749, filed on Oct. 19, 2011.

(51) Int. Cl.
*A61B 6/00* (2006.01)
*H05G 1/26* (2006.01)
(Continued)

(52) U.S. Cl.
CPC .............. *H05G 1/26* (2013.01); *G01N 23/046* (2013.01); *G01T 1/17* (2013.01); *G01T 1/24* (2013.01); *G01T 1/247* (2013.01); *G01T 7/005* (2013.01)

(58) Field of Classification Search
CPC ............ H05G 1/26; G01T 1/24; G01T 1/247; G01T 7/005; G01T 1/17; G01N 23/046
USPC .......... 378/4–20; 250/370.08, 370.09, 370.13
See application file for complete search history.

(56) References Cited

U.S. PATENT DOCUMENTS 5,804,833 A   9/1998   Stettner et al.
5,943,388 A   8/1999   Tumer
(Continued)

FOREIGN PATENT DOCUMENTS

WO   2009141760 A2   11/2009
WO   2011077302 A2   6/2011

OTHER PUBLICATIONS

Franchi, R., et al.; Photon counting X-ray imaging with CdTe pixel detectors based on XPAD2 circuit; 2006; Nuclear Instruments and Methods in Physics Research A; 563:249-253.
(Continued)

*Primary Examiner* — Courtney Thomas (57) ABSTRACT

An imaging system (300) includes a detector array (314) with direct conversion detector pixels that detect radiation traversing an examination region of the imaging system and generate a signal indicative of the detected radiation, a pulse shaper (316) configured to alternatively process the signal indicative of detected radiation generated by the detector array or a set of test pulses having different and known heights that correspond to different and known energy levels and to generate output pulses having heights indicative of the energy of the processed detected radiation or set of test pulses, and a thresholds adjuster (330) configured to analyze the heights of the output pulses corresponding to the set of test pulses in connection with the heights of set of test pulses and a set of predetermined fixed energy thresholds and generate a threshold adjustment signal indicative of a baseline based on a result of the analysis.

30 Claims, 9 Drawing Sheets

(51) Int. Cl.
*G01T 1/24* (2006.01)
*G01T 7/00* (2006.01)
*G01N 23/04* (2006.01)
*G01T 1/17* (2006.01)

(56) References Cited

U.S. PATENT DOCUMENTS

2007/0189443 A1* 8/2007 Walter ............... A61B 6/032
378/4
2010/0213353 A1 8/2010 Dierickx
2010/0329425 A1 12/2010 Guo et al.
2011/0036989 A1* 2/2011 Marks ............... G01T 1/17
250/370.08
2011/0096905 A1* 4/2011 Roessl ............... A61B 5/4869
378/62

OTHER PUBLICATIONS

Steadman, R., et al.; ChromAIX: A high-rate energy-resolving photon-counting ASIC for spectral Computed tomography; 2010; Proc. of SPIE; pp. 762220-8.

* cited by examiner

PHOTON COUNTING DETECTOR

CROSS REFERENCE TO RELATED APPLICATIONS

This application is a national filing of PCT application Serial No. PCT/IB2012/055554 filed Oct. 12, 2012, published as WO 2013/057645 A2 on Apr. 25, 2013, which claims the benefit of U.S. provisional application Ser. No. 61/548,749 filed Oct. 19, 2011, which is incorporated herein by reference.

The following generally relates to a photon counting detector and is described with particular application to computed tomography (CT); however, the following is also amenable to other imaging modalities.

A computed tomography (CT) scanner generally includes a rotating gantry rotatably mounted to a stationary gantry. The rotating gantry supports an X-ray tube and is configured to rotate around an examination region about a longitudinal. A detector array is located opposite the X-ray tube, across the examination region. The X-ray tube is configured to emit poly-energetic ionizing radiation that traverses the examination region (and a portion of an object or subject therein) and illuminates the detector array. The detector array includes a one or two dimensional array of detector pixels that detect the radiation and that generate signals indicative thereof. Each pixel is associated with a readout channel, which is used to convey a corresponding signal for further processing. A reconstructor reconstructs the processed signals, producing volumetric image data indicative of the examination region.

For spectral CT, the detector pixels have included direct conversion detector pixels. Generally, a direct conversion pixel includes a direct conversion material disposed between a cathode and an anode, with a voltage applied across the cathode and the anode. Photons illuminate the cathode, transferring energy to electrons in the direct conversion material, which creates electron/hole pairs, with the electrons drifting towards the anode. The anode, in response, produces the electrical signal output by the detector array. A pulse shaper processes the electrical signal and produces a pulse having an amplitude peak or height that is indicative of the energy of the detected radiation. An energy discriminator compares the height of the pulse with one or more energy thresholds. For each threshold, a counter counts the number of times the pulse height crosses the threshold. An energy-binner bins the counts in energy-ranges, thereby energy-resolving the detected radiation. The reconstructor reconstructs the binned signals using a spectral reconstruction algorithm.

Figure 1:
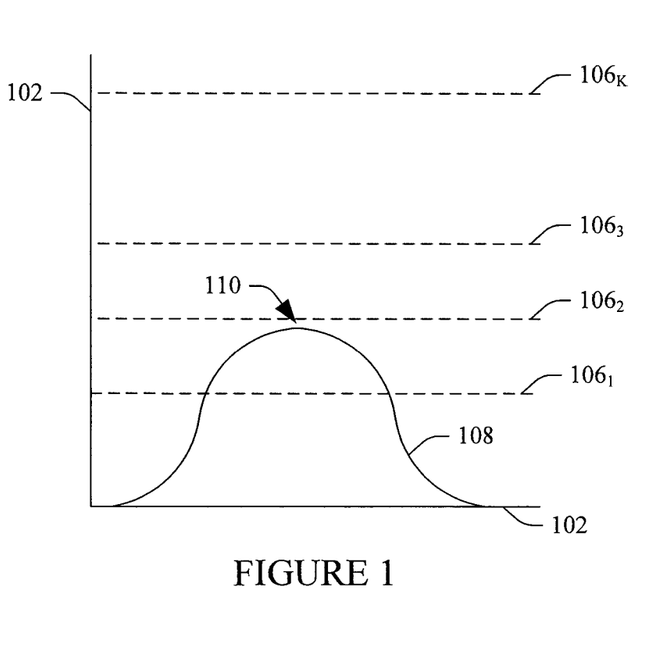
FIG. 1 illustrates a pulse generated by a pulse shaper in the absence of a baseline shift from direct conversion material of a direct conversion detector and in connection with a plurality of fixed energy thresholds.
Figure 2:
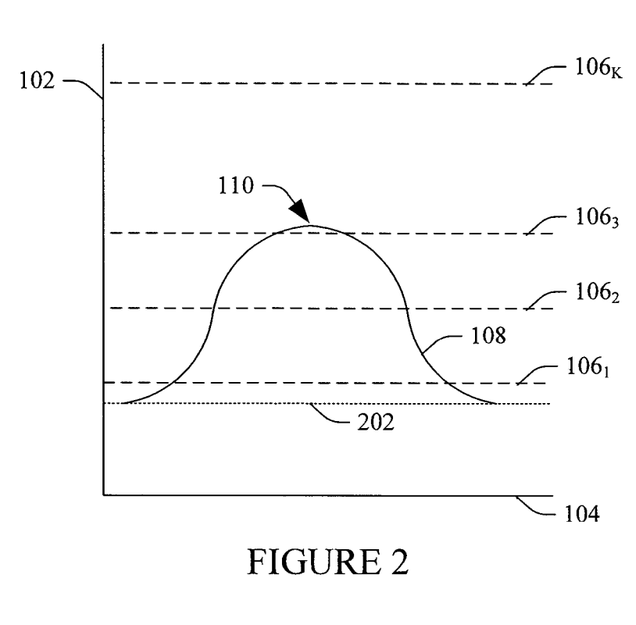
FIG. 2 illustrates the pulse generated by the pulse shaper in the presence of the baseline shift from the direct conversion material of the direct conversion detector and in connection with the plurality of the fixed energy thresholds.

Generally, direct conversion material can exhibit a baseline shift when irradiated with X-rays. As a consequence, the pulse output by the shaper is shifted up (or down, depending on the topology of the readout channel) and increases the relative height of the pulse. This baseline shift has included a low frequency component, which can be approximated as a DC component. Unfortunately, the baseline shift may lead to erroneously binning detected radiation into incorrect energy bins. An example of this is shown in connection with FIGS. 1 and 2, where a y-axis 102 represents amplitude, an x-axis 104 represents time, energy thresholds $106_1$, $106_2$, $106_3$, ..., $106_K$ (where K is an integer equal to or greater than one) represent the thresholds of the discriminator, and pulse 108 is the pulse generated by the shaper and has a peak 110. FIG. 1 shows the pulse 108 where there is no baseline shift. In this instance, the amplitude peak 110 lies between the thresholds $106_1$ and $106_2$. FIG. 2 shows the pulse 108 in the presence of a baseline shift 202. In this instance, the baseline shift 202 shifts the pulse up and the peak 110 now erroneously lies between the thresholds $106_3$ and $106_K$, and the discriminator will generate an output falsely indicating a higher energy than the actual energy of the pulse 108.

Furthermore, in photon-counting based spectral CT, a number of calibration steps are required to ensure accurate energy thresholds for energy discrimination. A fundamental part of such calibration steps is to perform a so-called "threshold scan," where the threshold level of each comparator of the discriminator is incrementally increased or decreased for a fixed input electrical pulse having known energy in order to find a relationship between the threshold position and the corresponding equivalent input energy. For routine use, such threshold scans have to be very fast. Generally, a threshold scan requires sweeping through all comparators for all detector pixels and reading out the detected number of counts at each discrete threshold position. This can be time consuming as it requires the detector controller to set up all the comparators for each position. By way of example, with a detector with 4×16 pixels, 4 energy thresholds, and 512 threshold levels, this may mean accessing the threshold registers 4×4× 16×512, or one hundred thirty one thousand and seventy-two (131,072), times. Unfortunately, the time required to perform a threshold scan may be unacceptable, particularly so when performing system calibration.

Aspects described herein addresses the above-referenced problems and others.

In one aspect, an imaging system includes a detector array, which includes a plurality of direct conversion detector pixels, that detects radiation traversing an examination region of the imaging system and generates a signal indicative of the detected radiation. The imaging system further includes a pulse shaper configured to alternatively process the signal indicative of detected radiation generated by the detector array or a set of test pulses having different and known heights that correspond to different and known energy levels and to generate output pulses having heights indicative of the energy of the processed detected radiation or set of test pulses. The imaging system further includes a thresholds adjuster configured to analyze the heights of the output pulses corresponding to the set of test pulses in connection with the heights of set of test pulses and a set of predetermined fixed energy thresholds and generate a threshold adjustment signal indicative of a baseline shift based on a result of the analysis.

In another aspect, a method includes determining a baseline shift in an output of a pulse shaper of an imaging system in response to processing a sequence of test input pulses, in which at least two of the input pulses have different heights, and heights of the input pulses correspond to known energy levels. The method further includes generating a signal indicative of the baseline shift. The method further includes generating a set of baseline shift adjusted energy discriminator thresholds based on the signal and a set of predetermined pulse energy discriminator thresholds of interest.

In another aspect, an imaging system includes a detector array, with a plurality of direct conversion detector pixels, that detects radiation traversing an examination region of the imaging system and generates a signal indicative of the detected radiation. The imaging system further includes a pulse shaper configured to process the signal and generate a pulse with a height indicative of the energy of the processed radiation. The imaging system further includes a discriminator with comparators configured to energy discriminate the pulse based on a set of thresholds and generate, for each energy threshold of the set of energy thresholds, a signal which indicates whether the height of the pulse exceeds the energy threshold. The imaging system further includes a counter that processes the signals output by the discriminator and counts, for each threshold, if the signal indicates that the height of the pulse exceeds the energy threshold. The imaging system further includes a threshold calibrator that generates energy threshold calibration data that defines a relationship between a set of calibration thresholds and input calibration electrical pulses having heights that correspond to known energy levels by injecting the input calibration electrical pulses into the shaper, incrementing or decrementing each of the calibration thresholds over corresponding predetermined ranges of threshold values one or more times for one or more data acquisition frames, and analyzing the corresponding count values of each threshold for each change in threshold value, using completion of one or more data acquisition frames as a trigger for incrementing or decrementing the calibration thresholds. The imaging system further includes an energy-binner that bins the counts corresponding to the processed signals into energy ranges based on the set of energy thresholds and the calibration data a relationship between the threshold levels and the energy of incoming radiation, thereby energy-resolving the detected radiation.

In another aspect, a method includes generating a set of calibration electrical pulses, each having a height that is different and that corresponds to known energy level. The method further includes injecting the set of calibration electrical pulses so that they are received at inputs of comparators of an energy discriminator. The method further includes generating a set of calibration thresholds for each of a plurality of data acquisition frames, each set including a threshold for each of the comparators, wherein the set of calibration thresholds is generated based on a current value of a scan counter which increments or decrements based on completion of at least one data acquisition frame. The method further includes energy discriminating each of the injected pulses each data acquisition frame using the respective energy thresholds for the respective comparator for the respective data acquisition frame. The method further includes generating energy threshold calibration data for each of the thresholds based on a relationship between each of the calibration electrical pulses and each of the calibration thresholds.

The invention may take form in various components and arrangements of components, and in various steps and arrangements of steps. The drawings are only for purposes of illustrating the preferred embodiments and are not to be construed as limiting the invention.

Figure 3:
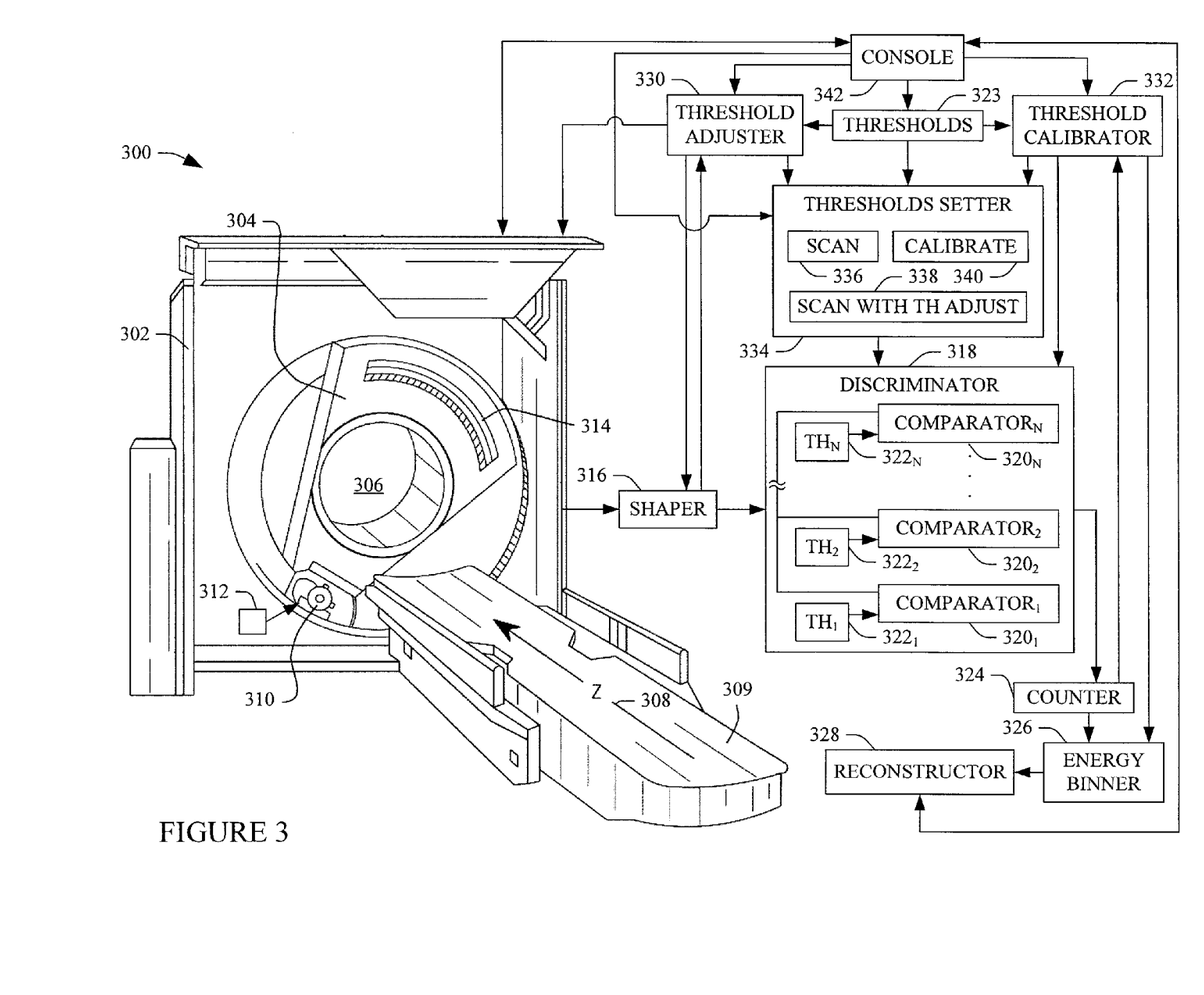
FIG. 3 schematically illustrates an example imaging system including at threshold adjustor and/or a threshold calibrator.

Initially referring to FIG. 3, an imaging system 300 such as a computed tomography (CT) scanner is schematically illustrated.

The imaging system 300 includes a stationary gantry 302 and a rotating gantry 304, which is rotatably supported by the stationary gantry 302. The rotating gantry 304 rotates around an examination region 306 about a longitudinal or z-axis 308.

A subject support 309, such as a couch, supports an object or subject in the examination region 306. The subject support 309 can be used to vertically and/or horizontally position the subject or object relative to the imaging system 300 before, during, and/or after scanning.

A radiation source 310, such as an X-ray tube, is supported by and rotates with the rotating gantry 304 around the examination region 306 about the longitudinal or z-axis 308. The radiation source 310 emits poly-energetic ionizing radiation that is collimated by a collimator or the like to produce a generally fan, wedge, or cone shaped radiation beam that traverses the examination region 306.

A source controller 312 transitions the radiation emission states between a state in which the source 310 emits radiation that traverses the examination region 306 and a state in which the source 310 does not emit radiation that traverses the examination region 306. This may include turning the source 310 "on"/"off," inserting/removing a filter from the path of radiation, applying/removing a grid voltage to a switching grid of the source 310 to inhibit/allow electrons to flow from the cathode to the anode of the source 306, etc.

A detector array 314 subtends an angular arc opposite the examination region 306 relative to the radiation source 310. The illustrated detector array 314 includes a one or two dimensional array of photon counting detector pixels such as direct conversion detector pixels, which include a direct conversion material such as cadmium telluride (CdTe), cadmium zinc telluride (CZT), and/or other direct conversion material. The detector array 314 detects radiation traversing the examination region 306 and generates a signal indicative thereof.

A pulse shaper 316 receives the signal generated by the detector array 314 and generates a pulse (e.g., a voltage or a current pulse) having a height or amplitude peak that is indicative of the energy of the corresponding incident detected radiation. Optionally, a pre-amplifier can be employed to amplify the signal prior to the pulse shaper 316 generating the pulse.

A discriminator 318 energy-discriminates the pulse based on predetermined energy thresholds $322_1$, $322_2$, ... $322_N$, where N is an integer equal to or greater than one (referred to collectively herein as thresholds 322), that correspond to different energy levels. The illustrated discriminator 318 includes comparators $320_1$, $320_2$, ..., $320_N$ (referred to collectively herein as comparators 322) that compare the height of a pulse from the shaper 316 respectively with the thresholds 322. Thresholds 323 include predetermined thresholds to be used as the thresholds 322. The discriminator 318 generates an output signal that indicates which of the thresholds 322 were exceeded by the height of the pulse.

A counter 324 counts, for each of the comparators 320, when an individual threshold is exceeded by a peak of a pulse, for each of the plurality of pulses.

An energy-binner 326 bins the counts into energy ranges based on a relationship between the threshold levels and the energy of incoming radiation, thereby energy-resolving the detected radiation.

A reconstructor 328 reconstructs the energy-binned signals via a spectral and/or a non-spectral reconstruction algorithm.

A threshold adjuster 330 determines a threshold adjustment signal that includes a value that compensates for a baseline shift, which may introduced at the shaper 316 by the direct conversion material of the detector array 314 and/or otherwise. As described in greater detail below, in one instance this includes injecting pulses having different heights corresponding to known energy levels into the shaper 316 during a sub-portion of a data acquisition frame in which radiation emission is interrupted, comparing the heights of the pulses output by the shaper 316 with the heights of the injected pulses in connection with the thresholds 323 and determining a threshold adjustment value based on the comparison, and providing the threshold adjustment signal so that the thresholds 323 can be adjusted for the baseline shift when discriminating scan data acquired during a different earlier sub-portion of the data acquisition frame.

A threshold calibrator 332 determines threshold calibration data that defines a relationship between each of the thresholds 322 and an energy level. As described in greater detail below, in one instance this includes automatically threshold scanning detector pixels of the detector array 314 based on a predetermined schedule (e.g., before each scan, once a day, etc.) by injecting fixed energy defined pulses into the comparators 320 and incrementing each of the thresholds 322 one or more sets of one or more data acquisition frames to cover a predetermined energy range of interest, determining the relationship between each threshold and the energy of the injected pulses based on the resulting counts, generating the calibration data based on this relationship, and providing the calibration data for energy binning pulses generated in response to detecting radiation emitted by the source 310. The threshold calibrator 332 can be very important since CT images can be very sensitive to pixel to pixel differences in the threshold values.

A threshold setter 334 includes various algorithms for setting the thresholds 322 of the comparators 320. In this example, the algorithms at least include one or more of a scan algorithm 336, which sets the thresholds 322 to the values of the thresholds 323, a scan with threshold (TH) adjust algorithm 338, which sets the thresholds 322 to the values of the thresholds 323 adjusted with the threshold adjustment signal output by the threshold adjuster 330, and a calibrate algorithm 340, which provides a series of incrementing or decrementing thresholds for sweeping each threshold 322 of each comparator 322 for each pixel of the detector array 314 during one or more threshold scans.

A general purpose computing system serves as an operator console 342, and includes an output device such as a display and an input device such as a keyboard, mouse, and/or the like. Software resident on the console 342 allows the operator to interact with the system 300. The console 342 also interacts with various components of the system 300. This may include sending a signal to the source controller 312 to transition the x-ray emission state, a signal to the threshold setter 334 to indicate which algorithm to use, signals to the threshold adjuster 330 and/or the threshold calibrator 332 to activate and/or deactivate the threshold adjuster 330 and/or the threshold calibrator 332, etc.

It is to be appreciated that at least one or more of the threshold adjuster 330, threshold calibrator 332, or the threshold setter 331 can be implemented via a processor (e.g., a micro processor) executing one or more computer readable instructions encoded or embedded on computer readable storage medium such as physical memory. Additionally or alternatively, at least one of the one or more computer readable instructions executed by the processor is carried by a carrier wave, a signal, or other non-computer readable storage medium such as a transitory medium.

It is also to be appreciated that in another embodiment one or more of the threshold adjuster 330 or the threshold calibrator 332 is omitted.

One or more of the shaper 316, the threshold adjuster 330, the threshold calibrator 332, the threshold setter, the discriminator 318, the counter 324, the energy binner 326, or the reconstructor 328 can be part of the system 300 (as shown) or separate therefrom.

Figure 4:
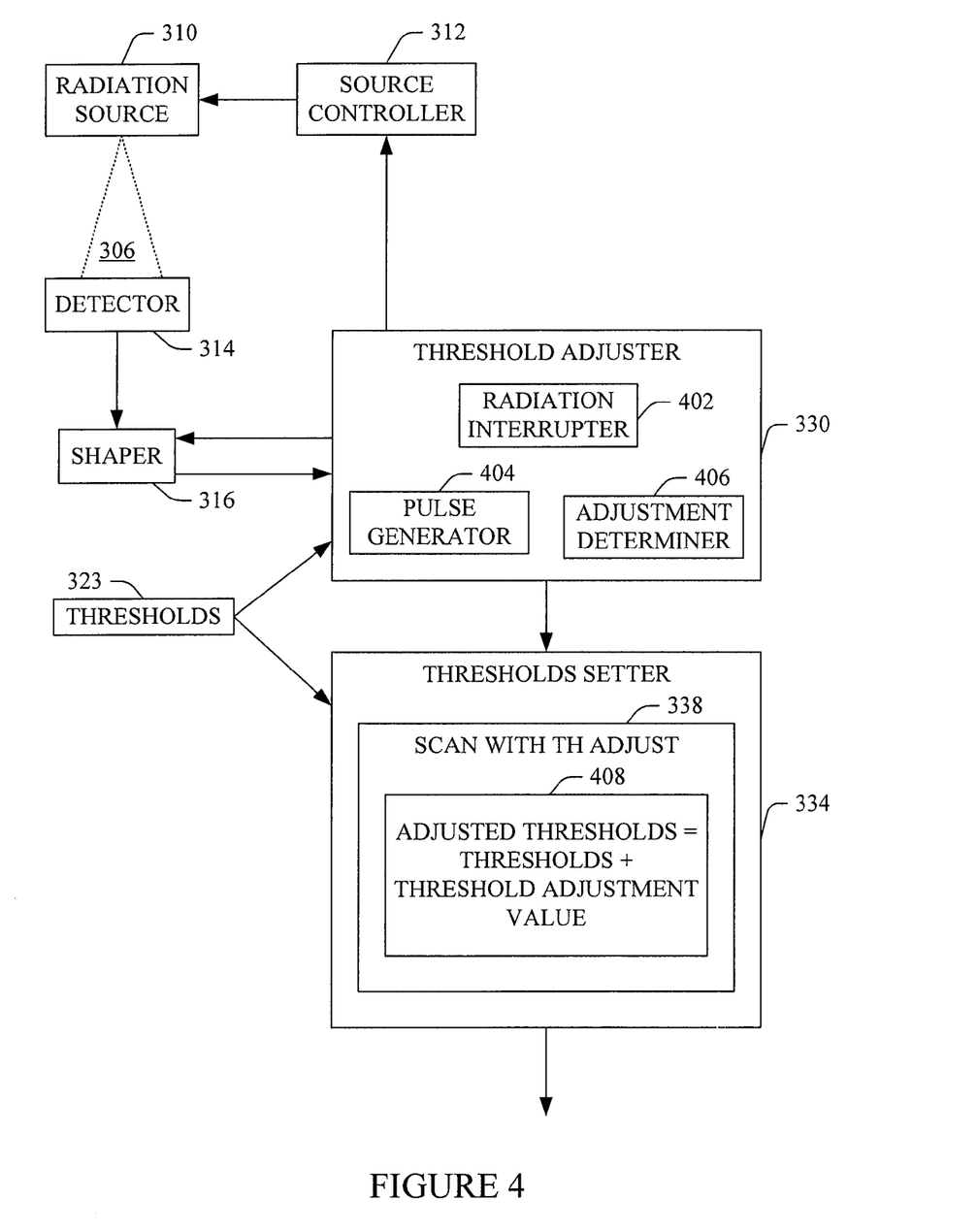
FIG. 4 schematically illustrates an example of the threshold adjustor.

FIG. 4 schematically illustrate a non-limiting example of the threshold adjuster 330 and the scan with TH adjust algorithm 338.

A radiation interrupter 402 is configured to convey a signal to the source controller 312 which causes the source controller 312 to interrupt radiation emission by the radiation source 310 through the examination region 306 for at least a predetermined time period such as a sub-portion of one or more data acquisition frames (integration periods). By way of non-limiting example, in one instance, the signal causes interruption of radiation emission for a time period in a range from approximately eighty (80) microseconds (μs) to approximately one hundred and twenty (120) μs at the end of one or more of the data acquisition frames.

While radiation emission is interrupted, a pulse generator 404 sequentially generates test pulses (e.g., a pulse train) having different and known amplitudes or heights, which correspond to predetermined energy levels. The pulse generator 404 conveys the generated pulses to the shaper 316 during the time period in which radiation emission is interrupted. By way of example, in one non-limiting instance, the pulse generator 404 can generate and convey pulses with a frequency on the order of ten (10) mega-Hertz (MHz) and a pulse duration of the order of ten (10) nanoseconds (ns) within the 80 to 120 μs time period, with an energy step of 0.5 keV, producing 1000 pulses in the time period, with about five (5) pulses of the same energy, between twenty (20) kiloelectron Volts (keV) and one hundred and twenty (120) keV.

It is to be understood that the above example is provided for explanatory purposes and is not limiting. As such, at least one of the time period, the frequency, the pulse duration, the energy step, the number of pulse, and/or the energy range can be different in other embodiments. This includes statics values, as in the above example, and/or varying values. For example, the energy step can be decreased (e.g., <0.5 keV) around energy levels of interest and increased (e.g., >0.5 keV) elsewhere.

An adjustment determiner 406 is configured to process the pulses generated by the shaper 316 corresponding to the injected sequence of test pulses. In one instance, this includes comparing the heights of the injected test pulses with the heights of the pulses generated by the shaper 316 corresponding to the injected sequence of test pulses in connection with the thresholds 323, and, based on the comparison, quantifying an energy shift therebetween which corresponds to a baseline, and generating a threshold adjustment signal including a threshold adjustment value that is based thereon.

Figure 5:
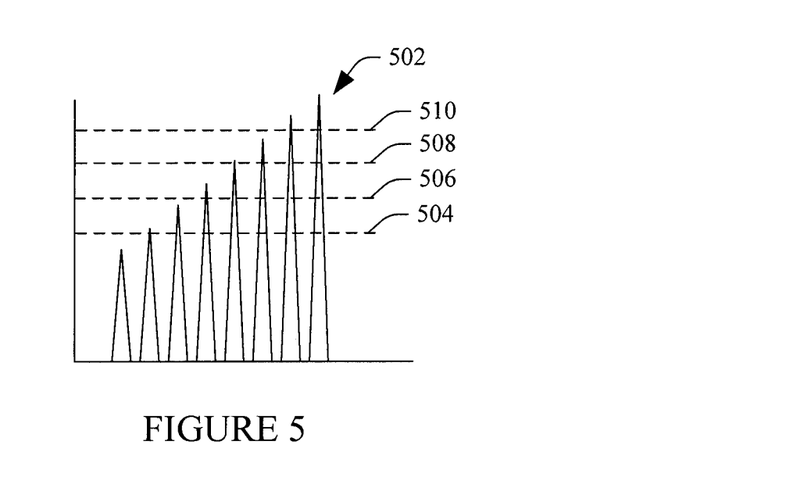
FIG. 5 illustrates a set of test pulses having different and known heights, which corresponds to a given energy, in connection with a predetermined fixed set of energy thresholds.
Figure 6:
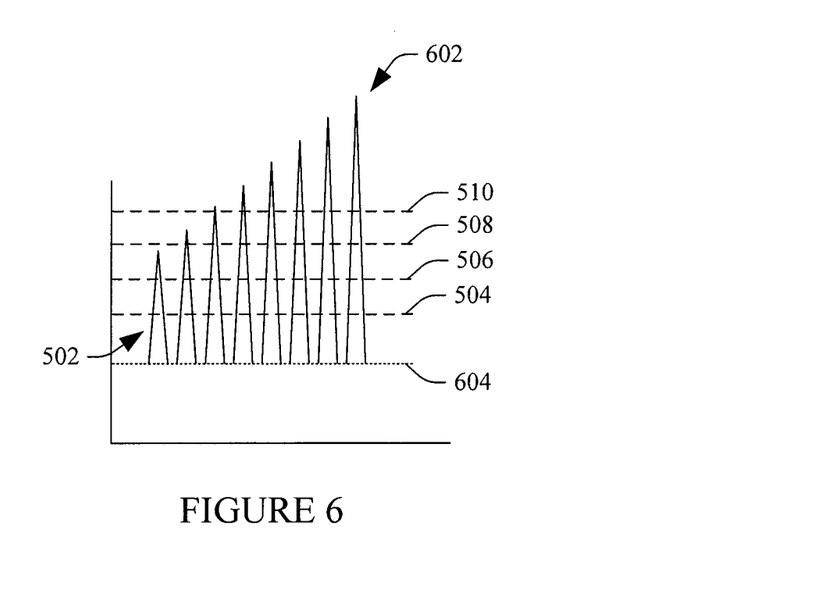
FIG. 6 illustrates pulses generated by the pulse shaper corresponding to the set of test pulses and shifted by the baseline, in connection with the predetermined fixed set of energy thresholds of FIG. 5.

By way of non-limiting example, FIG. 5 shows a set of test pulses 502 in connection with a set of thresholds 504, 506, 508, and 510, each pulse having a different peak height, which corresponds to a different energy level, with neighboring peak heights being separated by a fixed value (e.g., 0.5 keV), and FIG. 6 shows the same thresholds 504-510 along with pulses 602 generated by the shaper 316, which correspond to the injected sequence of test pulses 502 plus a non-zero baseline shift 604. In this example, without the baseline shift (FIG. 5), there are 2 pulses above the threshold 510, 3 pluses above the threshold 508, 5 pulses above the threshold 506, and 7 pulses above the threshold 504, and with the baseline shift 602 (FIG. 6), there are 6 pulses above the threshold 510, 7 pulses above the threshold 508, 8 pulses above the thresholds 506 and 504.

In this example, the adjustment determiner 406 iteratively increases the thresholds 504-510 by 1 keV (or different increment) until the above-noted pattern of FIG. 5 matches the pattern of FIG. 6 (and/or decrease the thresholds by 1 keV (or different increment) until the pattern of FIG. 6 matches the pattern of FIG. 5). Since, in this example, the energies of the electrical pulses generated by the pulse generator 404 are known and their differences are small, the adjustment determiner 406 can estimate the baseline shift with an accuracy on the order of about 1 keV plus the noise on the pulses and the thresholds. The adjustment determiner 406 can then determine the threshold adjustment value and signal based on the amount of change in keV which makes the patterns approximately equal.

Although the example of FIGS. 5 and 6 shows 8 pulses and 4 thresholds, it is to be understood that more or fewer pulses and/or more or fewer thresholds can alternatively be used. For example, in another embodiment the threshold adjustment can be determined based solely on the highest threshold since then the available "dynamic range" in terms of change of the number of detected pulses is highest. Generally, using more thresholds may improve the estimation of the baseline shift.

Returning to FIG. 4, the threshold setter 334 employs a scan with TH adjust algorithm 338 which at least includes an algorithm 408 which adds the threshold adjustment value to the thresholds 323 to generate a set of adjusted thresholds for the discriminator 318. The threshold setter 334 conveys the adjusted thresholds to the discriminator 318, which uses the adjusted thresholds to energy discriminate pulses. As a result, the discriminator 318 is able to energy discriminate the pulses more accurately relative to a configuration in which the threshold adjuster 330 is omitted or not used and the baseline shift from the direct conversion material is not accounted for.

In a variation of the above, the threshold adjustment value is additionally or alternatively used to adjust the height of the pulses output by the shaper 316 instead of just adjusting the thresholds 323.

In an alternative approach, a baseline restorer circuit configured to sense the baseline shift at the output of the shaper 316 can be used to control a current source at the input of the discriminator 318 such that the sensed baseline shift is reduced to zero.

Figure 7:
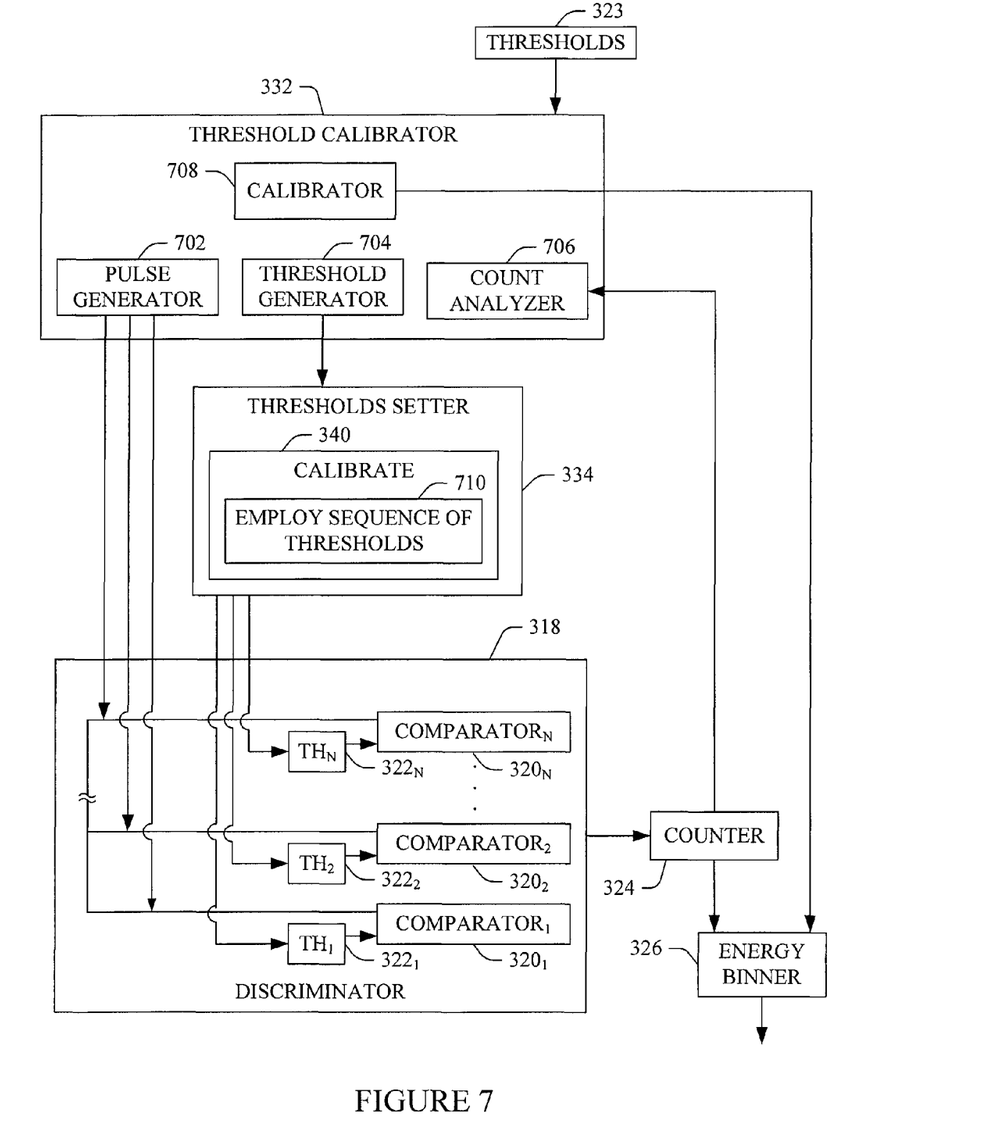
FIG. 7 schematically illustrates an example of the threshold calibrator, which at least includes a threshold generator.

FIG. 7 schematically illustrate a non-limiting example of the threshold calibrator 332 and the calibrate algorithm 340 in connection with the discriminator 318.

A pulse generator 702 generates calibration pulses for each of the comparators 320. The calibration pulses can be injected at the readout channels to the comparators 320 and/or elsewhere. The pulses for each of the comparators 320 have a different height which corresponds to the different energy levels of the different thresholds 323. In one instance, the pulse generator 702 and the pulse generator 404 (FIG. 4) are the same pulse generator.

A threshold generator 704 generates a set of thresholds for each of the thresholds 322. Non-limiting examples of suitable approaches for generating the sets of thresholds for the thresholds 322 of the different comparators 322 are described below in connection with FIGS. 8, 9, 10, 11, and 12.

The threshold setter 334 employs a calibrate algorithm 340 which at least includes an algorithm 710 that conveys the generated sets of thresholds for each of the thresholds 322 to the discriminator 318.

A count analyzer 706 analyzes the counts for each of the comparators 320 for each of the thresholds in the corresponding set of thresholds for each data acquisition frame. Theoretically, counts will be registered until the threshold 322 of a comparator 320 reaches a level of the energy of the pulse injected into to the comparator 320. At this point, the threshold level rises above the height of the energy of the pulse injected into to the comparator 320 and no more counts are registered. However, the actual profile will be more "s" shaped due to electronic noise of the counter 324 and/or other components.

A calibrator 708 generates calibration data for the comparators 320 based on the count analysis. The calibration data maps the thresholds 322 to the known energy injected calibration pulses based on a range around the thresholds level where the register counts drop to zero or near zero. The calibration data is provided to the energy binner 326, which uses the mapping to correctly energy bin the counts corresponding to detected radiation.

Figure 8:
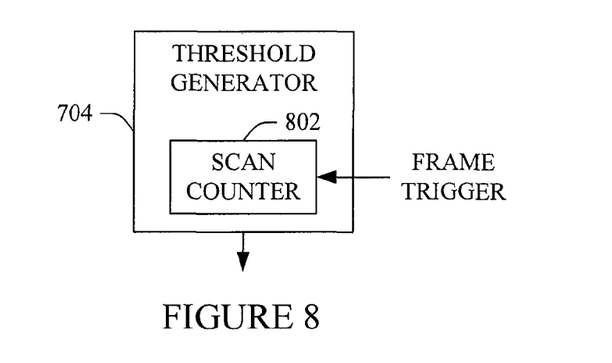
FIGS. 8, 9, 10, 11 and 12 schematically illustrate a non-limiting set of variations of the threshold generator.

Turning to FIG. 8, the threshold generator 704 employs a scan counter 802, which is incremented (or decremented) each data acquisition frame, to generate the sets of thresholds for the thresholds 322 for the different data acquisition frames. In this embodiment, the scan counter 802 is initially set to zero and is configured to increment by a predetermined step size up to an upper limit. The step size represents the change in the threshold value each data acquisition frame. By way of non-limiting instance, where the step size is set to increment the counter by a value corresponding to 1 keV, the scan counter 802 increments by 1 keV each data acquisition frame, for example, from 0 to 1 keV, from 1 keV to 2 keV, and so forth.

Figure 9:
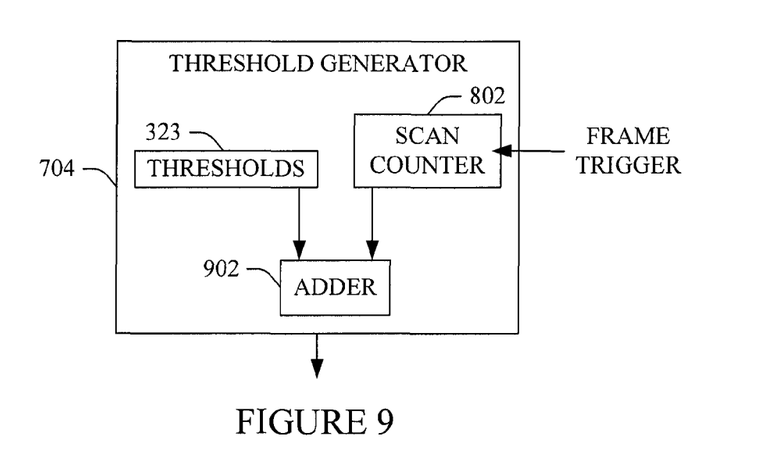

FIG. 9 is similar to FIG. 8 except that the threshold generator 704 further includes an adder 902. In this embodiment, the threshold generator 704 adds the output of the counter 802 for each data acquisition frame to the thresholds 323 to generate the sets of thresholds for the thresholds 322. With this embodiment, the threshold scan for each of the comparators 320 is performed starting with a different threshold value, namely, the values of the thresholds of interest 323 for the thresholds 322.

In one instance, the counter 802 starts counting up from zero (e.g., 0, 1, 2, 3, . . . ) in a positive direction and this count number is added to the previously stored threshold value. In another instance, the counter 802 can have negative and/or positive values and the adder 902 can add positive and/or negative numbers. In this instance, the threshold generator 704 can scan on both sides of the stored threshold value. By way of non-limiting example, where a threshold has a value of 45 (or other value), which is the value previously used for scanning, the counter 802 could count −10, −9, −8, . . . , −1, 0, 1, 2, 3, . . . , 9, 10 (or other range), which will produce output thresholds of 35, 34, . . . , 54, 55, which covers both sides of 45.

Figure 10:
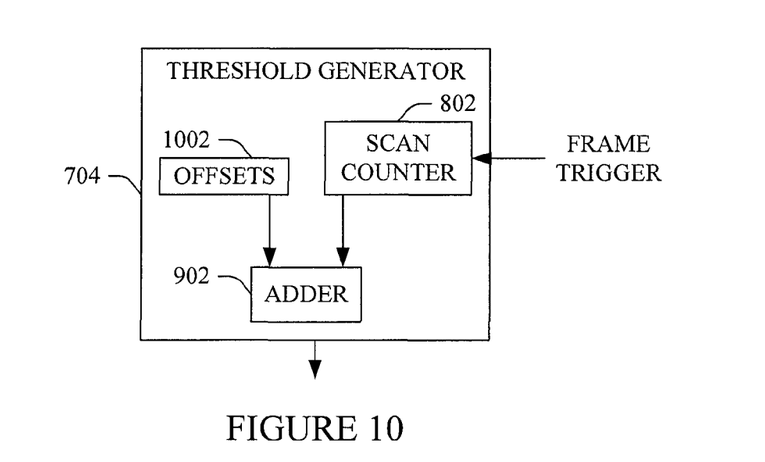

FIG. 10 is similar to FIG. 9 except that offsets 1002 are added to the scan counter 802 output each data acquisition frame instead of the thresholds of interest 323. Again, with this embodiment, the threshold scan for each of the comparators may begin at different threshold level. In addition, the starting point for each comparator 320 can be different than the threshold 323 for each comparator 320.

FIGS. 9 and 10 allow for decreasing the time of the threshold scan. By way of non-limiting example, where the discriminator 318 includes five (5) comparators 320 (N=5), the thresholds 323 or the offsets can be set, for example, respectively to 20 keV, 44 keV, 68 keV, 92 keV and 116 keV. In this instance, if the least significant bit (LSB) of the counter 802 corresponds to 0.5 keV, incrementing the scan counter 802 forty-eight (48) times would cover the entire dynamic range from 20-116 keV, instead of sweeping each of the thresholds 323 one hundred and ninety-two (192) times. That is, 48 increments at 0.5 keV per increment would transition the threshold 20 keV to 44 keV, and so forth.

Generally, the reduction in time theoretically can reduce threshold scan time to 1/Nth of the time. In another instance, the dynamic range is not split amongst the five comparators 320. That is, each or a subset of the five comparators can be configured to cover the entire dynamic range or a same subset of the entire dynamic range. For example, for a dynamic range from 20 to 116 keV, each or a subset of the five comparators can be swept one hundred and ninety-two times.

It is to be understood that the above range, increment, and/or number of comparators are not limiting and are provided for explanatory purposes. As such, in another embodiment, at least one of the dynamic range, the increment, or the number of comparators is different. In addition, the individual sub-ranges, which are separated by 24 keV in this example, do not have to be the same width, or a sub-range may not even exist. Moreover, the threshold scans of the individual ranges can be performed sequentially and/or concurrently.

Figure 11:
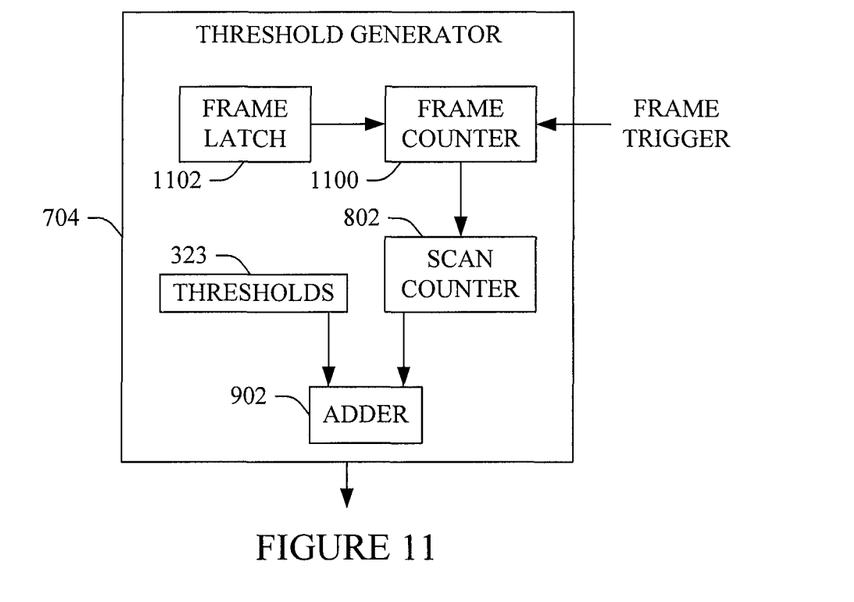

FIG. 11 is similar to FIG. 9 except that the threshold generator 704 further includes a frame counter 1100 and a latch 1102. Similar to FIG. 9, the set of thresholds is generated by the adding the thresholds 323 and the output of the scan counter 802. However, in this case, the scan counter 802 is not incremented each data acquisition frame.

Instead, the frame latch 1102 sets a desired number of frames that must occur prior to incrementing the scan counter 802 and the frame counter 1100 is triggered each data acquisition frame, and the frame counter 1100 triggers the scan counter 802 to increment upon lapse of the number of the data acquisition frame set by the latch 1102. The frame counter 1100 can either count up to or down from the desired number of data acquisition frames.

With this embodiment, each threshold scan is based on multiple data acquisition frames, which can be averaged or otherwise combined. In one instance, this may reduce noise relative to threshold scans based on a single frame (one frame per threshold position, which may exhibit noise levels that make it difficult to uniquely identify the threshold transitions).

Figure 12:
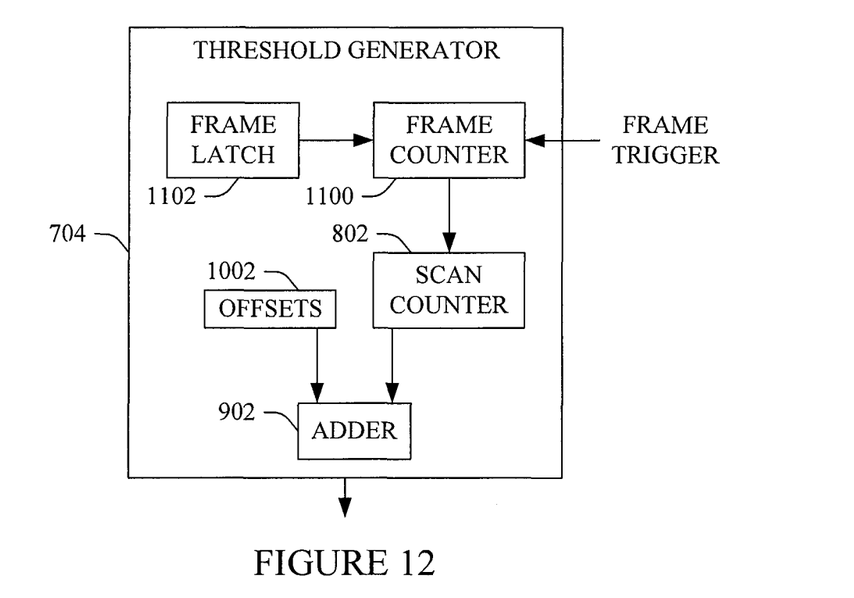

FIG. 12 is a similar to FIG. 11 except that the offsets 1002 are added with the scan counter 802 output instead of the thresholds 323, as described in connection with FIG. 10.

Figure 13:
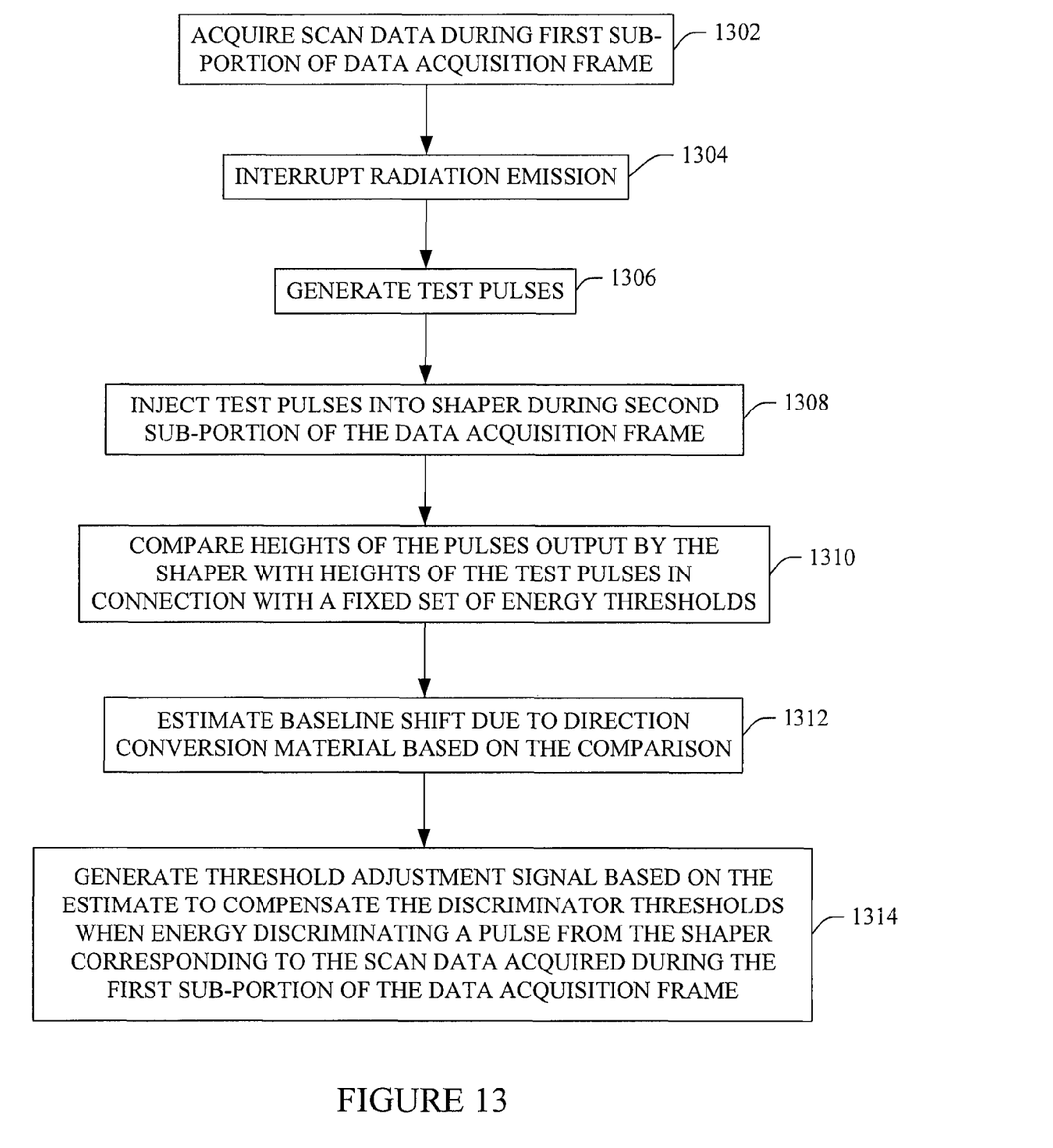
FIG. 13 illustrates a method for mitigating the introduction of a direct conversion material baseline shift in the pulse output by the pulse shaper.

FIG. 13 illustrates a method for mitigating a baseline shift in a data pulse generated by the pulse shaper 316.

It is to be appreciated that the ordering of the acts in the methods described herein is not limiting. As such, other orderings are contemplated herein. In addition, one or more acts may be omitted and/or one or more additional acts may be included.

At 1302, scan data corresponding to a scan of a subject or object is acquired during a first earlier sub-portion of a data acquisition frame while radiation is being emitted, and is processed by the pulse shaper 316, which generates a data pulse having a height indicative of the energy of the scan data.

At 1304, radiation emission is interrupted for a second later sub-portion of the data acquisition frame.

At 1306, different height test pulses are generated and sequentially fed to the pulse shaper during the second later sub-portion of the data acquisition frame. The different heights correspond to known energy levels.

At 1308, as each of the test pulses is fed to the pulse shaper 316, the pulse shaper 316 processes the test pulse and generates an output pulse having a height indicative of the energy of the test pulse.

At 1310, the heights of the output pulses of the shaper 316 and the heights of the test pulse are compared in connection with the thresholds 323.

At 1312, a threshold adjustment value is estimated based on the comparison. The threshold adjustment value corresponds to the baseline shift.

At 1314, a threshold adjustment signal is generated based on the threshold adjustment value and is used to adjust the thresholds 323 to compensate for the baseline shift when energy discriminating the data pulse corresponding to the scan data acquired during the first sub-portion the data acquisition frame.

Acts 1300 to 1314 are repeated one or more times for one or more data acquisition frames for one or more detector pixels of the detector array 314.

Figure 14:
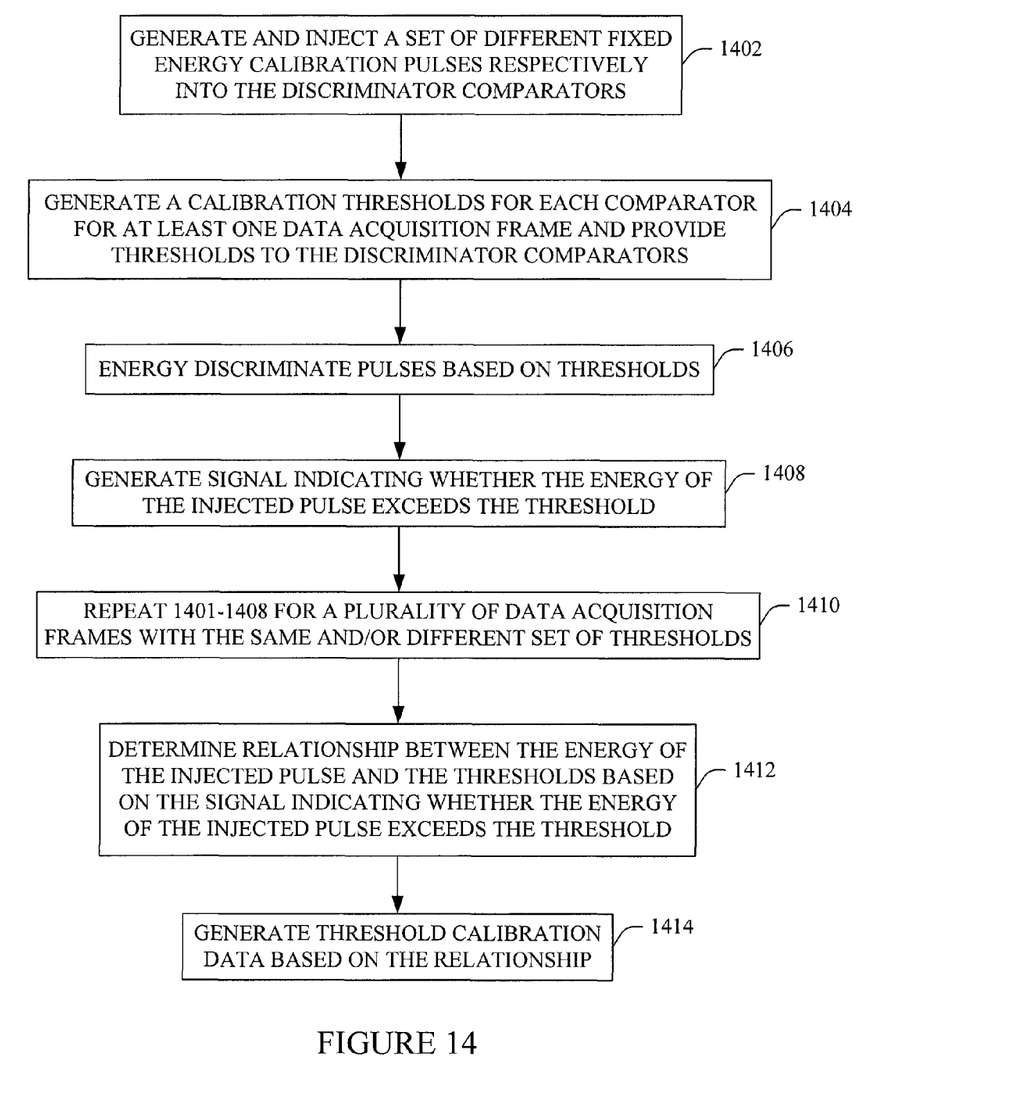
FIG. 14 illustrates a method for calibrating thresholds used in connection with a photon counting detector.

FIG. 14 illustrates a method for calibrating energy discriminator energy thresholds used in connection with a photon counting detector.

It is to be appreciated that the ordering of the acts in the methods described herein is not limiting. As such, other orderings are contemplated herein. In addition, one or more acts may be omitted and/or one or more additional acts may be included.

At 1402, a set of different fixed energy calibration pluses are generated and respectively injected in to the different comparators 320 of the discriminator 318 during a data acquisition frame.

At 1404, a set of calibration thresholds is generated and respectively provided to the different comparators 320 of the discriminator 318 during one or more data acquisition frame.

As discussed herein, the thresholds can be variously determined, for example, each data acquisition frame or after a predetermined number of data acquisition frames, and based on the scan counter 802, the thresholds 323, the offsets 1002, and/or the frame counter 1100 and frame latch 1102, which increments or decrements the calibration thresholds.

At 1406, the injected pulses are energy discriminated based on the calibration thresholds.

At 1408, the counter 324 generates a signal for each comparator 322 indicating whether the energy of the injected pulse exceeds the corresponding threshold.

At 1410, acts 1404 to 1408 are repeated one or more data acquisition frames with the same and/or one or more different sets of calibration thresholds.

At 1412, the signals indicative of whether the energy of the injected pulses exceeds the thresholds are used to determine a relationship between the thresholds 322 and the energy of the injected pulses.

At 1414, thresholds calibration data is generated based on the relationship.

As discussed herein, the above acts can be performed before each scan, after a predetermined number of scans, one a day, or based on some other criteria.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An imaging system, comprising:
a detector array, which includes a plurality of direct conversion detector pixels, that detects radiation traversing an examination region of the imaging system and generates a signal indicative of the detected radiation;
a pulse shaper configured to alternatively process the signal indicative of detected radiation generated by the detector array or a set of test pulses having different and known heights that correspond to different and known energy levels and to generate output pulses having heights indicative of the energy of the processed detected radiation or set of test pulses; and
thresholds adjuster configured to analyze the heights of the output pulses corresponding to the set of test pulses in connection with the heights of set of test pulses and a set of predetermined fixed energy thresholds and generate a threshold adjustment signal indicative of a baseline shift based on a result of the analysis.

2. The imaging system of claim 1, wherein the threshold adjustment signal includes a value that is determined based on a difference in the heights of the pulses and the test pulses.

3. The imaging system of claim 2, further comprising:
a threshold setter that determines a set of discriminator thresholds based on the threshold adjustment signal and a predetermined set of thresholds of interest.

4. The imaging system of claim 3, wherein the threshold adjustment signal adjusts the predetermined set of thresholds of interest to compensate for the baseline shift.

5. The imaging system of claim 3, further comprising:
a discriminator configured to energy discriminate the output pulses corresponding to the signal indicative of the detected radiation based on the determined set of discriminator thresholds.

6. The imaging system of claim 5, the discriminator, comprising:
a plurality of comparators, each comparing a height of the output pulse with a different threshold of the set of discriminator thresholds and generating a signal indicating whether the height of the output pulse exceeds the corresponding threshold.

7. The imaging system of claim 1, further comprising:
a radiation source configured to emit the radiation that traverses the examination region; and
a radiation source controller configured to transition the radiation source at least to a state in which radiation emission traversing the examination region is interrupted, and
the threshold adjuster, comprising:
a radiation interrupter that conveys a signal to the radiation source controller, which causes a state of radiation emission to transition to a state in which radiation emission traversing the examination region is interrupted;
a pulse generator that generates the set of test pulses and injects the pulses into the pulse shaper while radiation emission through the examination region is interrupted; and
an adjustment determiner that determines the threshold adjustment signal indicative of the baseline shift based on the result of the analysis.

8. The imaging system of claim 7, wherein the adjustment determiner iteratively adds one or more fixed energy increments to the set test pulses until the heights of the test pulses relative to the set of predetermined fixed energy thresholds and the heights of the output pulses corresponding to the set of test pulses relative to the set of predetermined fixed energy thresholds are approximately the same.

9. The imaging system of claim 7, wherein the adjustment determiner iteratively subtracts one or more fixed energy increments from the output pulses corresponding to the set of test pulses until the heights of the test pulses relative to the set of predetermined fixed energy thresholds and the heights of the output pulses corresponding to the set of test pulses relative to the set of predetermined fixed energy thresholds are approximately the same.

10. The imaging system of claim 8, wherein the threshold adjustment signal is determined based on a number of increments used to make the heights of the test pulses and the heights of the output pulses corresponding to the set of test pulses, relative to the set of predetermined fixed energy thresholds, approximately the same.

11. A method, comprising:
determining a baseline shift in an output of a pulse shaper of an imaging system in response to processing a sequence of test input pulses, in which at least two of the input pulses have different heights, and heights of the input pulses correspond to known energy levels;
generating a signal indicative of the baseline shift; and
generating a set of baseline shift adjusted energy discriminator thresholds based on the signal and a set of predetermined pulse energy discriminator thresholds of interest.

12. The method of claim 11, further comprising:
prior to determining the baseline shift,
interrupting data collection by the direct conversion detector array during a second stab-portion of a data acquisition frame, wherein scan data is collected during a first sub-portion of the data acquisition frame, wherein the first sub-portion occurs in time before the second sub-portion;
injecting the sequence of test pulses into the pulse shaper during the second sub-portion; and
generating the signal based on a difference in heights of the output of the shaper corresponding to the sequence of test pulses, the heights of the sequence of test pulses, and a set of fixed thresholds of interest, wherein the difference between the heights corresponds to the baseline shift.

13. The method of claim 12, further comprising:
iteratively increasing the heights of the sequence of test pulses by one or more fixed energy increments until the heights of the sequence of test pulses relative to the set of predetermined fixed energy thresholds is approximately equal to the heights of the output pulses corresponding to the set of test pulses relative to the set of predetermined fixed energy thresholds.

14. The method of claim 12, further comprising:
iteratively decreasing the heights of the output pulses corresponding to the set of test pulses by one or more fixed energy increments until the heights of the sequence of test pulses relative to the set of predetermined fixed energy thresholds is approximately equal to the heights of the output pulses corresponding to the set of test pulses relative to the set of predetermined fixed energy thresholds.

15. The method of claim 13, wherein the threshold adjustment signal is determined based on a number of increments used to make the heights of the test pulses relative to the set of predetermined fixed energy thresholds and the heights of the output pulses corresponding to the set of test pulses relative to the set of predetermined fixed energy thresholds approximately equal.

16. An imaging system, comprising:
a detector array, with a plurality of direct conversion detector pixels, that detects radiation traversing an examination region of the imaging system and generates a signal indicative of the detected radiation;
a pulse shaper configured to process the signal and generate a pulse with a height indicative of the energy of the processed radiation;
a discriminator with comparators configured to energy discriminate the pulse based on a set of thresholds and generate, for each energy threshold of the set of energy thresholds, a signal which indicates whether the height of the pulse exceeds the energy threshold;
a counter that processes the signals output by the discriminator and counts, for each threshold, if the signal indicates that the height of the pulse exceeds the energy threshold;
a threshold calibrator that generates energy threshold calibration data that defines a relationship between a set of calibration thresholds and input calibration electrical pulses having heights that correspond to known energy levels by injecting the input calibration electrical pulses into the shaper, incrementing or decrementing each of the calibration thresholds over corresponding predetermined ranges of threshold values one or more times for one or more data acquisition frames, and analyzing the corresponding count values of each threshold for each change in threshold value, using completion of one or more data acquisition frames as a trigger for incrementing or decrementing the calibration thresholds; and
an energy-binner that bins the counts corresponding to the processed signals into energy ranges based on the set of energy thresholds and the calibration data that defines a relationship between the threshold levels and the energy of incoming radiation, thereby energy-resolving the detected radiation.

17. The imaging system of claim 16, the threshold calibrator, comprising:
a scan counter configured to increment or decrement after each data acquisition frame; and
a threshold generator that generates the set of calibration thresholds for a next data acquisition frame based on a current value of the scan counter after a data acquisition frame.

18. The imaging system of claim 17, wherein a same calibration threshold value is employed for all of the thresholds in the set of calibration thresholds for a data acquisition frame.

19. The imaging system of claim 16, the threshold calibrator, further comprising:
a different fixed energy level value for each of the comparators; and
an adder,
wherein the threshold generator generates the set of calibration thresholds for the next data acquisition frame by adding, via the adder, the current value of the scan counter to the different fixed energy value, for each of the comparators, thereby creating a set of calibration thresholds in which each threshold has a different value.

20. The imaging system of claim 19, wherein the different fixed energy level value for a threshold corresponds to a predetermined energy threshold level of interest for the threshold.

21. The imaging system of claim 19, wherein the different fixed energy level value for a threshold corresponds to an offsets of interest for the threshold.

22. The imaging system of claim 19, the threshold calibrator, further comprising:
a frame counter that generates a trigger signal after a predetermined number of data acquisition frames and conveys the trigger signal to the scan counter, which increments or decrements in response to receiving the trigger signal, and the threshold generator determines the set of calibration thresholds for the next data acquisition frame based on the current value of the scan counter after each data acquisition frame.

23. A method, comprising:
generating a set of calibration electrical pulses, each having a height that is different and that corresponds to known energy level;
injecting the set of calibration electrical pulses respectively into inputs of comparators of an energy discriminator;
generating a set of calibration thresholds for each of a plurality of data acquisition frames, each set including a threshold for each of the comparators, wherein the set of calibration thresholds is generated based on a current value of a scan counter which increments or decrements based on completion of at least one data acquisition frame;
energy discriminating each of the injected pulses each data acquisition frame using the respective energy thresholds for the respective comparator for the respective data acquisition frame; and
generating energy threshold calibration data for each of the thresholds based on a relationship between each of the calibration electrical pulses and each of the calibration thresholds.

24. The method of claim 23, wherein the scan counter is incremented or decremented each data acquisition frame.

25. The method of claim 24, wherein the scan counter is incremented or decremented after a predetermined number of data acquisition frames.

26. The method of claim 25, further comprising:
adding a predetermined fixed value to the current value of the scan counter to generate the energy threshold calibration data.

27. The method of claim 26, wherein the fixed value is the same for each comparator.

28. The method of claim 26, wherein the fixed value is different for at least two comparators.

29. The method of claim 23, further comprising:
determining the calibration data for each pixel of a photon counting detector array of an imaging system.

30. The method of claim 23, further comprising:
automatically determining the calibration data at least before a scan of an object or subject.

* * * * *